United States Patent
Kaneko

(10) Patent No.: US 11,554,395 B2
(45) Date of Patent: Jan. 17, 2023

(54) SAFETY CABINET

(71) Applicant: Hitachi Industrial Equipment Systems Co., Ltd., Tokyo (JP)

(72) Inventor: Takeshi Kaneko, Tainai (JP)

(73) Assignee: Hitachi Industrial Equipment Systems Co., Ltd., Tokyo (JP)

( * ) Notice: Subject to any disclaimer, the term of this patent is extended or adjusted under 35 U.S.C. 154(b) by 312 days.

(21) Appl. No.: 16/768,186

(22) PCT Filed: Feb. 4, 2019

(86) PCT No.: PCT/JP2019/003884
§ 371 (c)(1),
(2) Date: May 29, 2020

(87) PCT Pub. No.: WO2019/207892
PCT Pub. Date: Oct. 31, 2019

(65) Prior Publication Data
US 2020/0290100 A1 Sep. 17, 2020

(30) Foreign Application Priority Data
Apr. 24, 2018 (JP) ............................. JP2018-083422

(51) Int. Cl.
*B08B 17/00* (2006.01)
*B01D 46/00* (2022.01)
(Continued)

(52) U.S. Cl.
CPC .......... *B08B 17/00* (2013.01); *B01D 46/0043* (2013.01); *B01L 1/00* (2013.01); *B08B 15/023* (2013.01)

(58) Field of Classification Search
CPC .......... B08B 17/00; B08B 15/023; B01L 1/00
(Continued)

(56) References Cited

U.S. PATENT DOCUMENTS

2018/0001315 A1   1/2018 Kaneko et al.

FOREIGN PATENT DOCUMENTS

CN       202453304 U      9/2012
DE   102013000768 A1 *   7/2014   ............. B08B 15/02
(Continued)

OTHER PUBLICATIONS

Chinese-language Office Action issued in Chinese Application No. 201980007194.9 dated May 27, 2021 (eight (8) pages).
(Continued)

*Primary Examiner* — Avinash A Savani
*Assistant Examiner* — Dana K Tighe
(74) *Attorney, Agent, or Firm* — Crowell & Moring LLP

(57) ABSTRACT

An object of the present invention is to provide a safety cabinet that allows a clearer observation of contamination of an operation stage surface. In order to realize the object, the safety cabinet is configured to include an operation space including an operation stage; a front panel formed in a front surface of the operation space; an operation opening provided in a lower portion of the front panel; a suction port that is provided in the vicinity of the operation opening on a front side of the operation stage to lead downward; and an air circulation path through which air suctioned from the suction port flows along a lower portion, a back surface, and an upper portion of the operation space, in which the operation stage is made of a transparent material, and a light source is provided to irradiate the operation stage with a light from a side of the operation stage, which is opposite to the operation space.

5 Claims, 4 Drawing Sheets

(51) Int. Cl.
 B01L 1/00 (2006.01)
 B08B 15/02 (2006.01)
(58) Field of Classification Search
 USPC .......................................................... 454/57
 See application file for complete search history.

(56) References Cited

FOREIGN PATENT DOCUMENTS

| | | |
|---|---:|---|
| JP | 4-344447 A | 12/1992 |
| JP | 2003-75367 A | 3/2003 |
| JP | 2009-76390 A | 4/2009 |
| JP | 2010-156620 A | 7/2010 |
| JP | 2016-75608 A | 5/2016 |
| JP | 2016-165249 A | 9/2016 |
| JP | 2017-78527 A | 4/2017 |
| WO | WO 2017/081572 A1 | 5/2017 |

OTHER PUBLICATIONS

International Search Report (PCT/ISA/210) issued in PCT Application No. PCT/JP2019/003884 dated Apr. 23, 2019 with English translation (four (4) pages).

Japanese-language Written Opinion (PCT/ISA/237) issued in PCT Application No. PCT/JP2019/003884 dated Apr. 23, 2019 (four (4) pages).

* cited by examiner

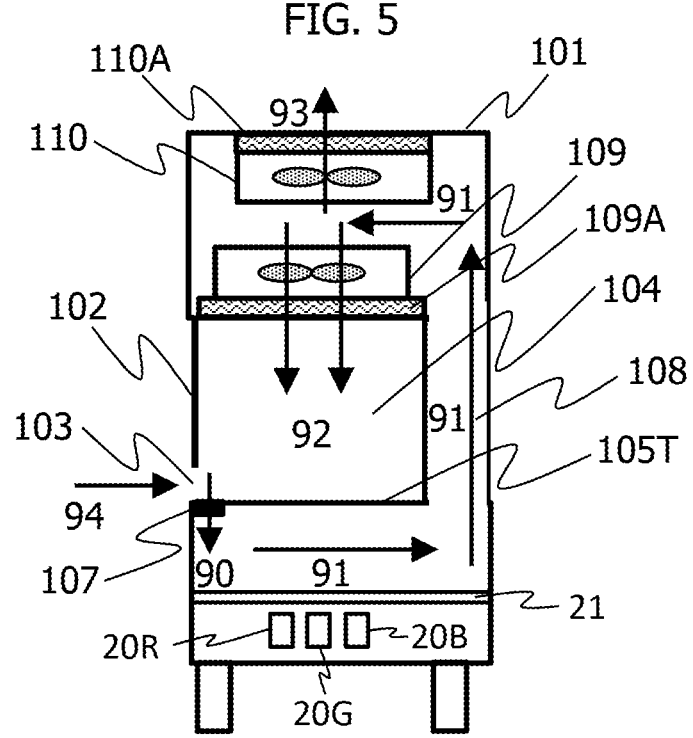
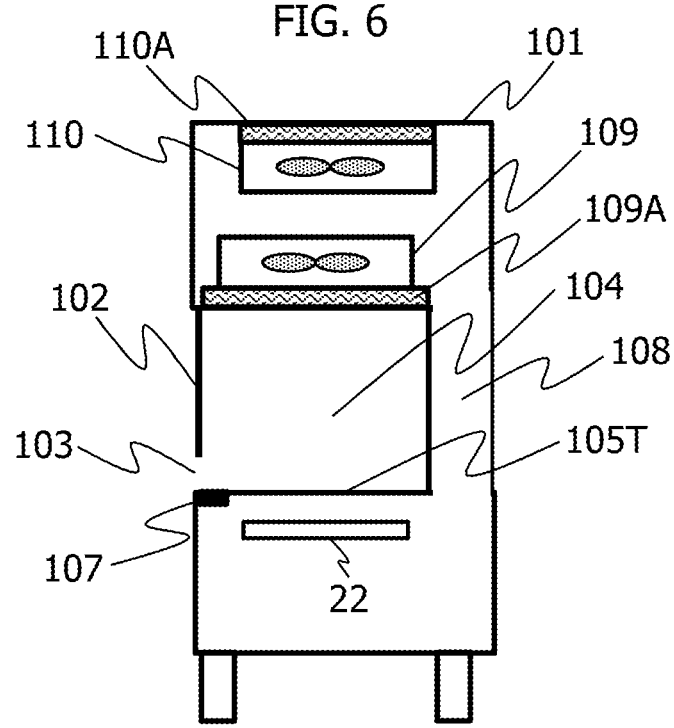

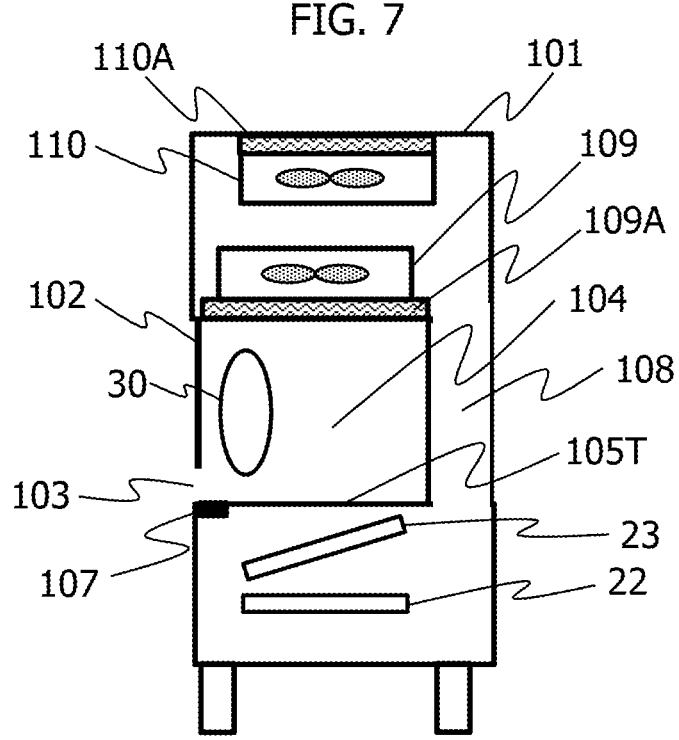

SAFETY CABINET

TECHNICAL FIELD

The present invention relates to a safety cabinet that uses an air barrier to eliminate a contamination risk from outside.

BACKGROUND ART

In the related art, in the fields of industries such as medicine and pharmaceuticals, a safety cabinet is used as a countermeasure against biohazards. In the safety cabinet, an air barrier is provided and an operation is performed in a partitioned space including an opening portion in a part thereof, and thus the safety cabinet has the isolation capability to be able to protect specimen from sundry bacteria from outside.

Patent Document 1 and Patent Document 2 disclose the background art of the technical field. Patent Document 1 discloses a safety cabinet that includes an open duct including a coupling portion connected to an exhaust port of the safety cabinet, an opening portion which is different from the coupling portion and into which air flows, and an exhaust duct. The safety cabinet includes a differential pressure sensor that detects a difference between a pressure in a space where the open duct is disposed and a pressure in the open duct, and detection means for outputting detection signal when an absolute value of the differential pressure sensor is a predetermined threshold value or less. In addition, Patent Document 2 discloses a technique where see-through windows are provided in a part of a back wall or a side wall of an operation space of the safety cabinet and a part of a main body rear wall or a main body side wall of the safety cabinet which is separated from the back wall or the side wall by a circulation flow path, to allow an operator to see through both walls, a display device is installed in an outside portion of the see-through window, and the operator inserts the arms from a front opening portion of the safety cabinet perform an operation while seeing the operation space from a front shutter.

CITATION LIST

Patent Document

Patent Document 1: JP 2017-078527 A
Patent Document 2: JP 2016-165249 A

SUMMARY OF THE INVENTION

Problems to be Solved by the Invention

In the safety cabinets disclosed in Patent Document 1 and Patent Document 2 which maintain an internal purity to allow an operation to be safely performed, the operator performs the operation on an operation stage in the operation space. However, generally, the operation stage made of a stainless steel material, and it is difficult to visually confirm contamination of an operation stage surface, which is a problem.

The present invention has been made in light of the foregoing problem, and an object of the present invention is to provide a safety cabinet that allows a clearer observation of contamination of an operation stage surface.

Solutions to Problems

The present invention has been made in light the background art and the problem described above, and according to one example of the present invention, there is provided a safety cabinet including: an operation space including an operation stage; a front panel formed in a front surface of the operation space; an operation opening provided in a lower portion of the front panel; a suction port that is provided in the vicinity of the operation opening on a front side of the operation stage to lead downward; and an air circulation path through which air suctioned from the suction port flows along a lower portion, a back surface, and an upper portion of the operation space, in which the operation stage is made of a transparent material, and a light source is provided to irradiate the operation stage with a light from a side of the operation stage, which is opposite to the operation space.

Effects of the Invention

According to the present invention, it is possible to provide a safety cabinet that allows a clearer observation of contamination of an operation stage surface.

BRIEF DESCRIPTION OF THE DRAWINGS

FIG. 5 is a schematic side view of a safety cabinet in a second embodiment.

FIG. 6 is a schematic side view of a safety cabinet in a third embodiment.

FIG. 7 is a schematic side view of a safety cabinet in a fourth embodiment.

MODE FOR CARRYING OUT THE INVENTION

Hereinafter, embodiments of the present invention will be described with reference to the drawings.

First Embodiment

First of all, initially, a safety cabinet in the related art which is the premise of the present embodiment will be described.

Figure 1:
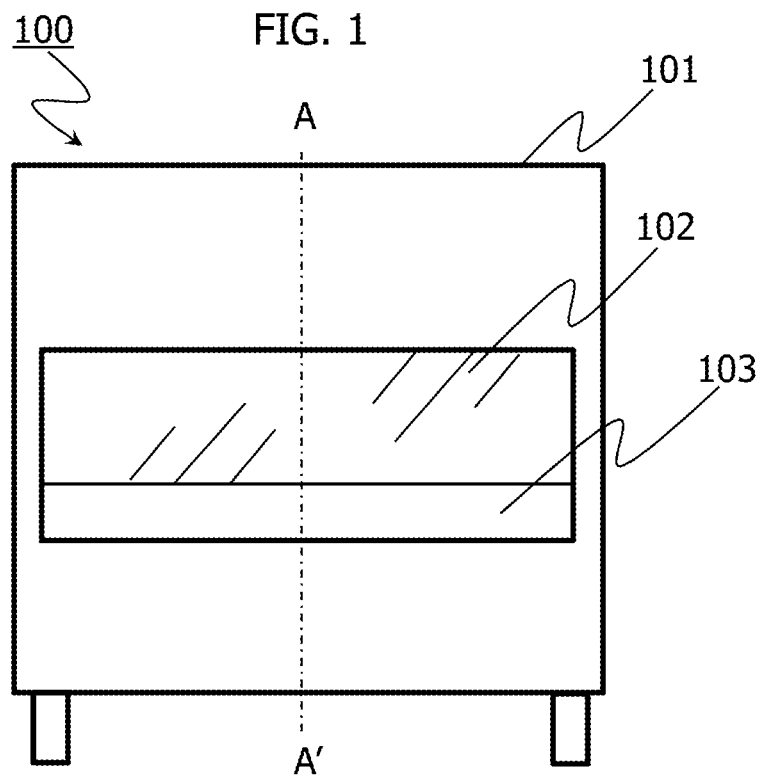
FIG. 1 a schematic front view of a safety cabinet in the related art.
Figure 2:
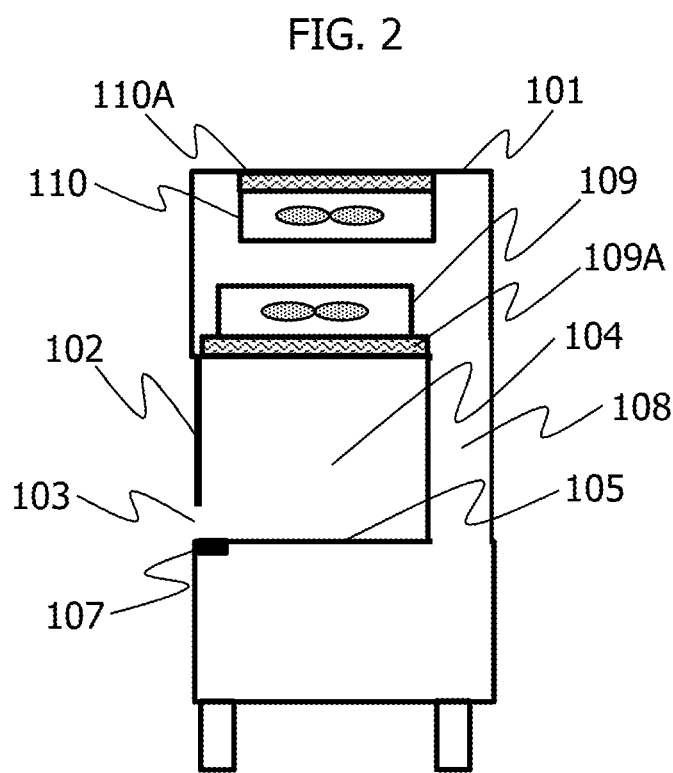
FIG. 2 is a schematic side view of the safety cabinet when a cross section A-A' in FIG. 1 is seen from right.

FIG. 1 illustrates a schematic front view of the safety cabinet. In addition, FIG. 2 illustrates a schematic side view of the safety cabinet when a cross section A-A' in FIG. 1 is seen from right.

An opening is provided in a central region of a housing 101 of a safety cabinet 100, and an operation space 104 is provided therebehind. A front panel 102 is provided on a front surface side of the operation space 104 to block an upper portion of the opening, an operation opening 103 is provided below the front panel 102, and an operator inserts the hands into the operation space 104 from the operation opening 103 to perform an operation. The front panel 102 is made of a transparent material such as a glass, and the operator can see an operation through the front panel.

An operation stage 105 which is substantially flat is provided in a bottom surface of the operation space 104, and the operator performs an operation on the operation stage. A suction port 107 is provided near the operation opening 103 on a front side of the operation stage 105 to lead downward. The suction port 107 is formed as, for example, a slit that extends along the operation opening 103 in a rightward and leftward direction of the housing. A back flow path 108 leading from the suction port 107 to an upper portion of the housing is provided on a back surface side of the operation space 104.

A blowout side fan filter unit (FFU) 109 is provided on an upper side of the operation space 104. The blowout side FFU 109 includes a fan that is rotated by a motor and a filter that removes microparticles, for example, HEPA filter 109A, and blows out purified air, from which the microparticles have been removed, into the operation space 104. An exhaust side fan filter unit (FFU) 110 is provided in the upper portion of the housing 101, and removes microparticles from a part of air with a filter, for example, a HEPA filter 110A to exhaust the part of air outside the device.

Figure 3:
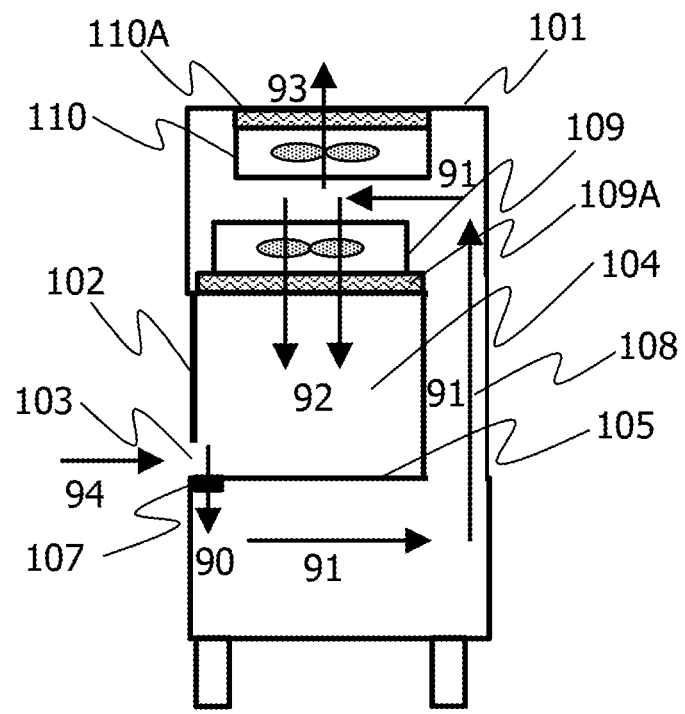
FIG. 3 is a view illustrating an air flow during operation of the safety cabinet in FIG. 2.

In FIG. 3, an air flow during operation of the safety cabinet is indicated by arrows. An air 90 which is suctioned from the suction port 107 on a front surface side of the operation stage 105 is blown, as indicated by reference sign 91, into the operation space 104 from the blowout side FFU 109 through a lower portion of the housing, the back flow path 108, and the upper portion of the housing. Since purified air from which the microparticles have been removed by the HEPA filter 109A of the blowout side FFU 109 is blown into the operation space 104, the operation space 104 is maintained in a purified state. In this case, when only an air flow denoted by reference sign 92 flows into the operation space 104, air in the operation space may leak outside, which is a concern. For this reason, the exhaust side FFU 110 is provided to discharge a part of air outside through the HEPA filter 110A. Accordingly, the pressure in the operation space decreases, and an air flow 94 which is to be introduced from outside to inside through the operation opening 103 below the front panel 102 is generated. When the air flow 94 flows into the operation space as it is, the purity of the operation space deteriorates. However, the air volume of the air flow 92 which is blown out into the operation space from the blowout side FFU 109 and the air volume of an air flow 93 which is exhausted outside from the exhaust side FFU 110 are properly controlled, so that all of the air flow 94 flowing in from the operation opening 103 and the majority of the air flow 92 blown into the operation space are suctioned from the suction port 107. Therefore, an atmospheric barrier (air barrier) which prevents the air flow 94 from flowing into the operation space 104 from the operation opening 103 is formed by the air flow 92 which is blown out into the operation space 104. Accordingly, it is possible to realize an equilibrium state where the air from outside does not contaminate the operation space 104 and non-purified inside air does not leak outside.

Accordingly, even when the operator inserts the hands into the operation space 104 through the operation opening 103 to perform an operation, it is possible to realize the maintenance of the purity and the prevention of contamination.

Here, generally, the operation stage 105 is made of a stainless steel material, and it is difficult to visually confirm contamination of an operation stage surface, which is a problem.

Therefore, in order to solve the problem, the present embodiment employs a configuration where the operation stage surface is made transparent and a back surface of the operation stage is provided with a multicolor light source. Hereinafter, the configuration will be described in detail.

Figure 4:
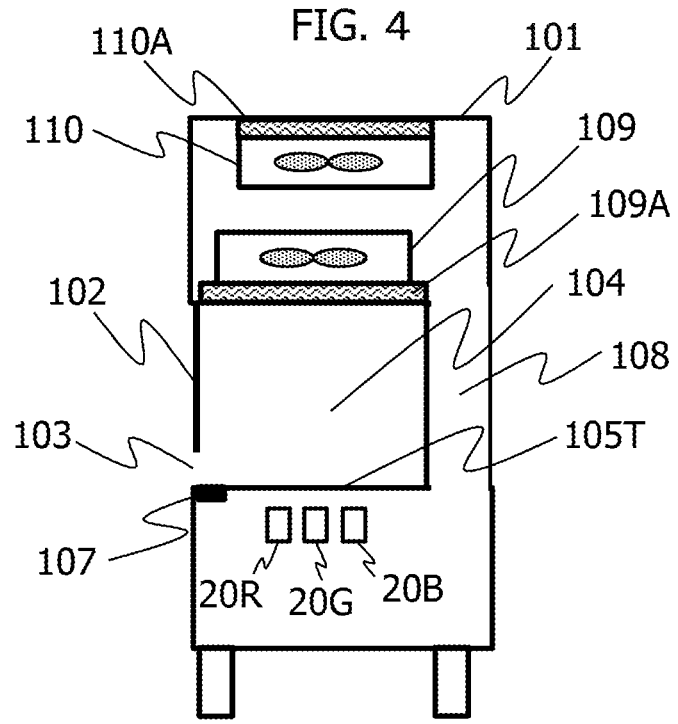
FIG. 4 is a schematic side view of a safety cabinet in a first embodiment.

FIG. 4 is a schematic side view of the safety cabinet in the present embodiment. In FIG. 4, the same reference signs are assigned to components having the same functions as those in FIG. 2, and descriptions thereof will be omitted. The point of difference of FIG. 4 from FIG. 2 is that an operation stage 105T which is transparent is provided as the operation stage and light sources 20R, 20G, and 20B are disposed on a back surface of the operation stage 105T. The light sources 20R, 20G, and 20B are light sources emitting colors of R, G, and B.

As illustrated in FIG. 4, the operation stage 105T is irradiated with a light from the light sources 20R, 20G, and 20B from the back surface of the operation stage 105T, namely, a side of the operation stage 105T which is opposite to the operation space 104, so that contaminants on the operation stage 105T are revealed. Therefore, it is possible to more clearly observe contamination on the operation stage 105T. Incidentally, depending on the type of contaminant, the way the contaminant is revealed is changed according the wavelength of an irradiating light source, and thus the operation stage surface is irradiated with light while the sources 20R, 20G, and 20B are switched.

Incidentally, it is preferable that the operation stage 105T is made of a glass material to be transparent; however, the material is not limited thereto and may be transparent acrylics, plastics, or the like. In addition, it is preferable that LEDs capable of emitting a single color are used as the light sources 20R, 20G, and 20B; however, the light sources are not limited thereto. In addition, in FIG. 4, the light sources for the colors of R, G, and B are separately disposed; however, one light source may emit multiple colors.

In addition, the light sources 20R, 20G, and 20B may be disposed to irradiate the entirety of the operation stage 105T with a light. A plurality of point light sources may be two-dimensionally disposed in a matrix pattern, a plurality of linear light sources may be disposed side by side, or a planar light source may be used.

As described above, according to the present embodiment, it is possible to provide the safety cabinet that allows a clearer observation of contamination of the operation stage surface.

Second Embodiment

FIG. 5 is a schematic side view of a safety cabinet in the present embodiment. In FIG. 5, the same reference signs are assigned to components having the same functions as those in FIGS. 2 and 3, and descriptions thereof will be omitted. The point of difference of FIG. 5 from FIGS. 2 and 3 is that a transparent panel 21 is disposed below an air circulation path provided in a lower portion of the housing 101 and the light sources 20R, 20G, and 20B are provided below the transparent panel 21.

In FIG. 5, a space is provided as the air circulation path below the operation stage 105T. For this reason, when the light sources are disposed in the region, there is a possibility that the air flow is hindered by the sizes or the like of the light sources. For this reason, the transparent panel 21 is disposed below the air circulation path, and the light sources 20R, 20G, and 20B are disposed below the transparent panel 21. Accordingly, the operation stage 105T is irradiated via the transparent panel 21 with a light from the light sources 20R, 20G, and 20B, and since the light sources do not hinder the air flow in the air circulation path, the purity of the operation space 104 can be maintained.

Third Embodiment

FIG. 6 is a schematic side view of a safety cabinet in the present embodiment. In FIG. 6, the same reference signs are assigned to components having the same functions as those in FIG. 4, and descriptions thereof will be omitted. The point of difference of FIG. 6 from FIG. 4 is that a flat display 22 is provided as a light source on the back surface of the operation stage 105T.

As illustrated in FIG. 6, when the flat display 22 such as a liquid crystal display or an organic EL (OLED) display is provided as a light source, the flat display 22 can be used as a light source for inspection to observe contamination of the operation stage surface, and can serve to display information such as an operation procedure or a checklist in a normal operation state of the safety cabinet. An operator can cause the flat display 22 to display the information such as the operation procedure or the checklist, and confirm the information through the operation stage 105T which is transparent.

Incidentally, in combination with the configuration of the second embodiment, the present embodiment may employ a configuration where the transparent panel 21 is disposed below the air circulation path provided in the lower portion of the housing 101 and the flat lisp 22 is provided below the transparent panel 21.

Fourth Embodiment

FIG. 7 is a schematic side view of a safety cabinet in the present embodiment. In FIG. 7, the same reference signs are assigned to components having the same functions as those in FIG. 6, and descriptions thereof will be omitted. The point of difference of FIG. 7 from FIG. 6 is that a deflecting body 23 is provided between the operation stage 105T and the flat display 22.

As illustrated in FIG. 7, when information is displayed, owing to the effect of the deflecting body 23, the information displayed on the flat display 22 can be displayed via the operation stage 105T in a display region 30 of a space positioned diagonally forward in the safety cabinet (in the illustrated case, on a front side in the operation space 104). A microlens array can be used as the deflecting body 23. In addition, it is possible to use a laminated medium obtained by extending a mirror pattern which is fine in a thickness direction in one direction and changing the angle of the mirror pattern a plurality of times. In addition, a transparent panel may be provided between the deflecting body 23 and the flat display 22. Accordingly, the information such as the operation procedure or the checklist can be displayed diagonally forward in the safety cabinet, and thus the information can be displayed near the line of sight of the operator. As a result, the effect of being easy to see the displayed content is realized.

In addition, for display in the space, a motion sensor may be used to operate or select a button on the display. Accordingly, there is no direct contact by the hand, and thus the effect of preventing contamination is realized.

In addition, when the flat display 22 is used as a light source for inspection observe contamination of the operation stage surface, a mechanism which changes the angle of the flat display 22 provided to cause the deflecting body 23 perform a display on the operation stage 105T; and thereby, it is possible to efficiently observe contamination of the operation stage surface.

Incidentally, the present embodiment may be combined with the second embodiment.

The embodiments have been described above; however, the present invention is not limited to the embodiments and includes various modification examples. For example the embodiments have been described in detail to facilitate the understanding of the present invention, and the present invention is not necessarily limited to including all of the described configurations. In addition, a part of a configuration of an embodiment can be substituted with a configuration of another embodiment. In addition, a configuration of another embodiment can also be added to a configuration of an embodiment. In addition, another configuration can be added to, deleted from, or substituted with a part of the configuration of each embodiment.

REFERENCE SIGNS LIST 20R, 20G, 20B Light source
21 Transparent panel
22 Flat display
23 Deflecting body
30 Display region
100 Safety cabinet
101 Housing
102 Front panel
103 Operation opening
104 Operation space
105, 105T Operation stage
107 Suction port
108 Back flow path
109 Blowout side fan filter unit (FFU)
109A Blowout side HEPA filter
110 Exhaust side fan filter unit (FFU)
110A Exhaust side HEPA filter

The invention claimed is:

1. A safety cabinet comprising:
an operation space including an operation stage;
a front panel formed in a front surface of the operation space;
an operation opening provided in a lower portion of the front panel;
a suction port that is provided in the vicinity of the operation opening on a front side of the operation stage to lead downward; and
an air circulation path through which air suctioned from the suction port flows along a lower portion; a back surface, and an upper portion of the operation space, wherein
the operation stage is made of a transparent material,
the safety cabinet further includes a light source provided to irradiate the operation stage with a light from a side of the operation stage, which is opposite to the operation space,
a transparent panel is disposed below the air circulation path in the lower portion of the operation space,
the light source emits a single color of light and is disposed below the transparent panel, and
the transparent panel extends a same length as the lower portion of the operation space.

2. The safety cabinet according to claim 1,
wherein the single color of light is R G, or B to irradiate the operation stage with the light while switching the colors.

3. The safety cabinet according to claim 1,
wherein the light source is a flat display and the flat display serves as a light source that irradiates the operation stage with a light and displays information.

4. The safety cabinet according to claim 3,
wherein a deflecting body is provided between the operation stage and the flat display to display an information display of the flat display in a space.

5. The safety cabinet according to claim 4, wherein an angle of the flat display is adjusted so as to cause the deflecting body to perform a display on the operation stage.

\* \* \* \* \*